US012697148B2

(12) United States Patent
Biedermann et al.

(10) Patent No.: US 12,697,148 B2
(45) Date of Patent: Aug. 4, 2026

(54) ROD SYSTEM INCLUDING AT LEAST TWO RODS AND CONNECTOR DEVICE FOR RODS

(71) Applicant: BIEDERMANN TECHNOLOGIES GMBH & CO. KG, Donaueschingen (DE)

(72) Inventors: Timo Biedermann, Trossingen (DE); Heiko Koller, Bad Endorf (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/303,365

(22) Filed: Apr. 19, 2023

(65) Prior Publication Data

US 2023/0329760 A1 Oct. 19, 2023

Related U.S. Application Data

(63) Continuation of application No. 17/378,229, filed on Jul. 16, 2021, now Pat. No. 11,653,955.

(Continued)

(30) Foreign Application Priority Data

Jul. 22, 2020 (EP) ..................................... 20187183

(51) Int. Cl.
*A61B 17/70* (2006.01)
(52) U.S. Cl.
CPC ........ *A61B 17/705* (2013.01); *A61B 17/7025* (2013.01)

(58) Field of Classification Search
CPC .. A61B 17/705; A61B 17/683; A61B 17/8605
See application file for complete search history.

(56) References Cited

U.S. PATENT DOCUMENTS 2,022,025 A * 11/1935 Bradford, Jr. .......... D02G 3/362
29/4.55
5,330,473 A 7/1994 Howland
(Continued)

FOREIGN PATENT DOCUMENTS

WO WO 2009/001978 A1 12/2008

OTHER PUBLICATIONS

European Search Report for Application No. 20 187 183.7, dated Jan. 19, 2021, 3 pages.

*Primary Examiner* — Tessa M Matthews
(74) *Attorney, Agent, or Firm* — Womble Bond Dickinson (US) LLP

(57) ABSTRACT

A rod system, in particular, for the spine, includes a first rod, a second rod, and a connector for connecting the first rod and the second rod. The connector includes a main body defining a first rod seat configured to hold the first rod in a fixed manner and a second rod seat configured to accommodate a second rod, and a fixation member and a closure member that are interchangeably mountable to the main body. When the fixation member is mounted to the main body, the fixation member is engageable with the portion of the second rod to hold the second rod in a fixed manner relative to the main bod, while when the closure member is mounted to the main body, the closure member is configured to hold the second rod to the main body in a slidable manner.

13 Claims, 14 Drawing Sheets

Related U.S. Application Data

(60) Provisional application No. 63/055,100, filed on Jul. 22, 2020.

(56) References Cited

U.S. PATENT DOCUMENTS

| | | | |
|---|---|---|---|
| 7,699,874 B2 | 4/2010 | Young | |
| 7,803,174 B2 | 9/2010 | Denis et al. | |
| 7,806,912 B2 | 10/2010 | Lawton et al. | |
| 8,246,657 B1 | 8/2012 | Samuel | |
| 8,940,021 B2 | 1/2015 | James | |
| 8,961,572 B2 | 2/2015 | Kim et al. | |
| 9,339,307 B2 | 5/2016 | McClintock et al. | |
| 9,408,639 B2 | 8/2016 | Miladi | |
| 9,918,748 B2 | 3/2018 | Kalfas et al. | |
| 10,561,454 B2 | 2/2020 | Lee et al. | |
| 10,610,262 B2 | 4/2020 | Castelein et al. | |
| 2005/0228378 A1 | 10/2005 | Kalfas et al. | |
| 2006/0058789 A1 | 3/2006 | Kim et al. | |
| 2006/0206114 A1 | 9/2006 | Ensign et al. | |
| 2006/0233597 A1* | 10/2006 | Ensign | A61B 17/7037 403/177 |
| 2007/0123860 A1* | 5/2007 | Francis | A61B 17/7044 606/250 |
| 2007/0173825 A1* | 7/2007 | Sharifi-Mehr | A61B 17/705 606/272 |
| 2007/0270818 A1 | 11/2007 | Rezach | |
| 2010/0049242 A1* | 2/2010 | Bacher | A61B 17/29 606/205 |
| 2010/0256683 A1 | 10/2010 | Lott et al. | |
| 2010/0280552 A1 | 11/2010 | Lee | |
| 2013/0018429 A1* | 1/2013 | George | A61B 17/7002 606/86 R |
| 2013/0268004 A1 | 10/2013 | Rathbun | |
| 2014/0303674 A1 | 10/2014 | Sasing | |
| 2015/0080953 A1 | 3/2015 | Otte et al. | |
| 2018/0338782 A1* | 11/2018 | Castelein | A61B 17/7049 |
| 2019/0269445 A1* | 9/2019 | Singh | A61B 17/8047 |
| 2019/0336178 A1 | 11/2019 | Finn et al. | |

* cited by examiner

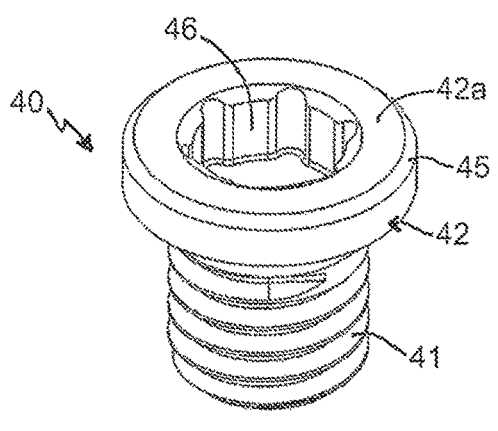
Fig. 14
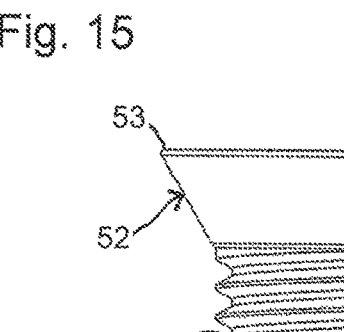
Fig. 15
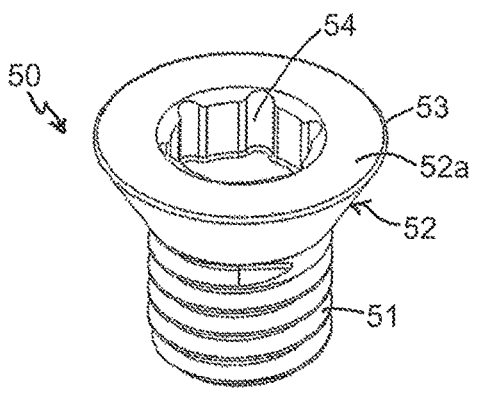
Fig. 16
Fig. 17
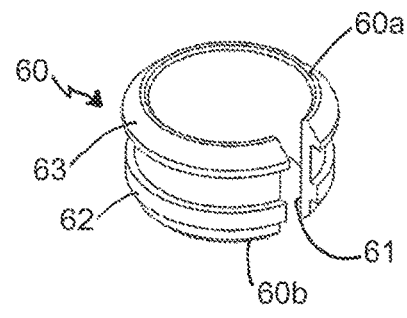
Fig. 18
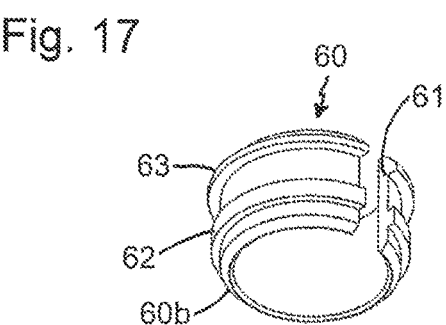
Fig. 19
Fig. 20
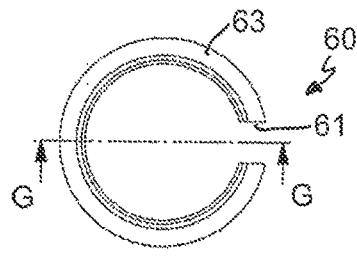
Fig. 21

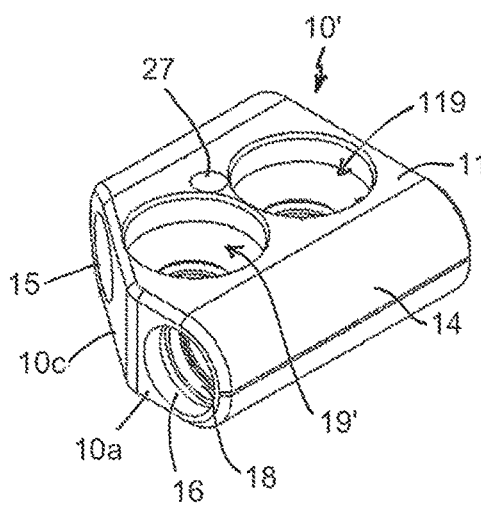
Fig. 24
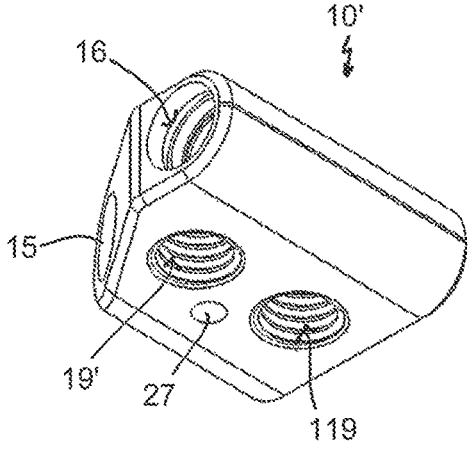
Fig. 25
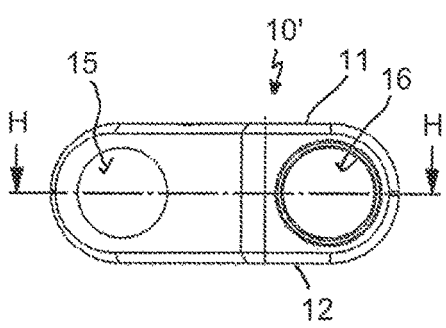
Fig. 26
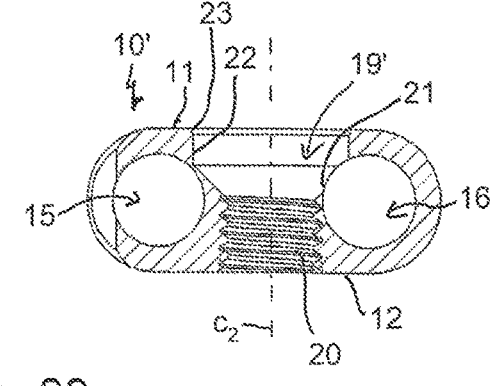
Fig. 27
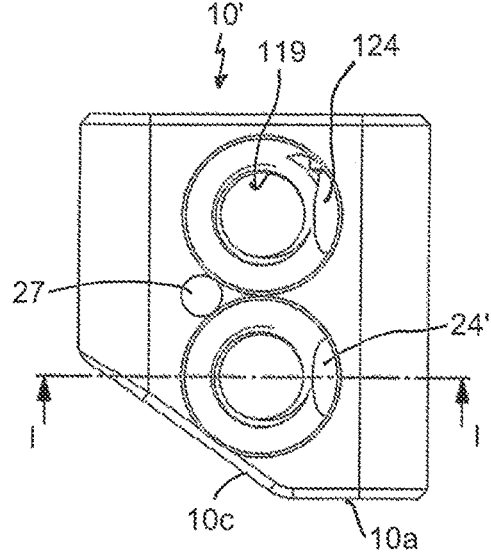
Fig. 28
Fig. 29

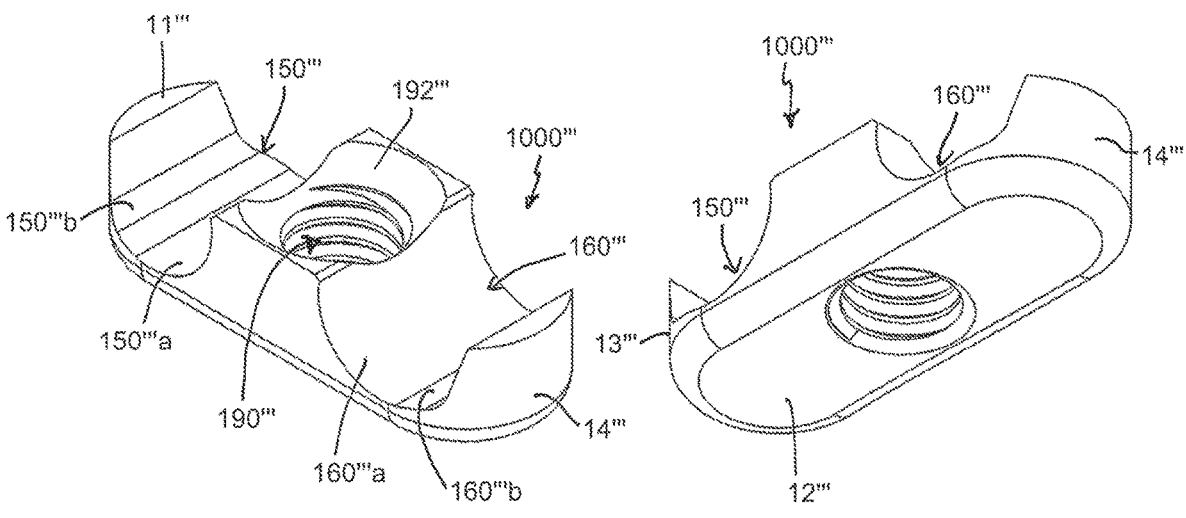
Fig. 40
Fig. 41
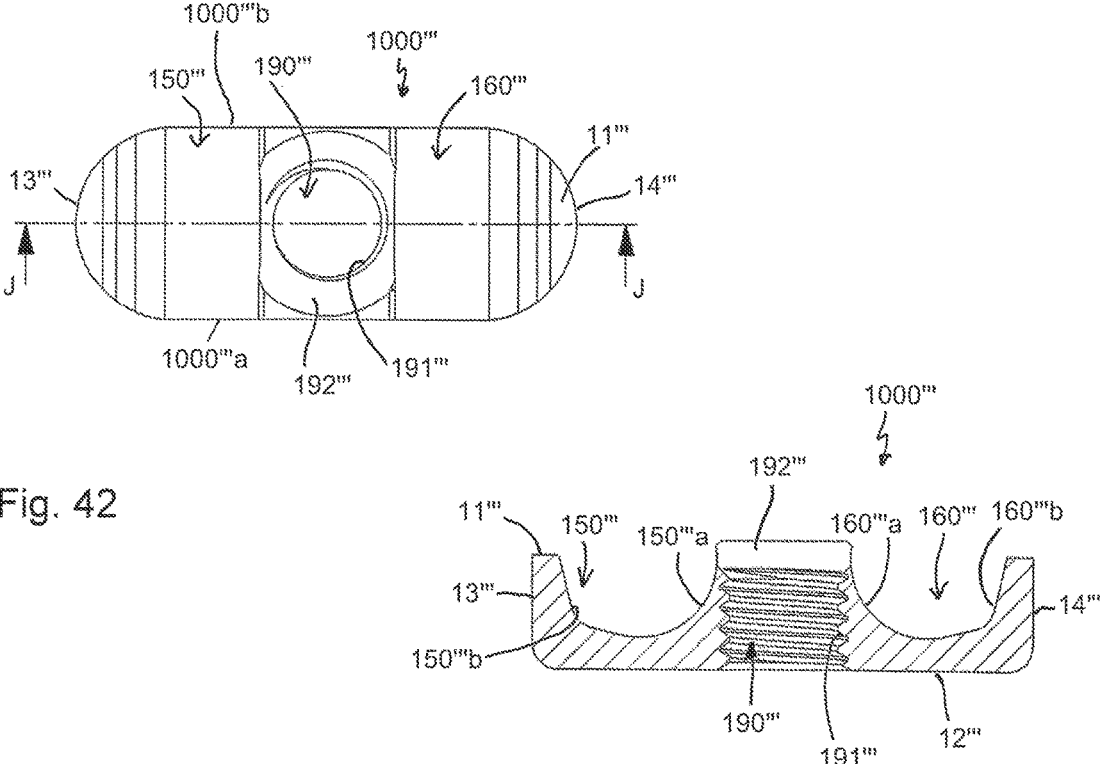
Fig. 42
Fig. 43

ROD SYSTEM INCLUDING AT LEAST TWO RODS AND CONNECTOR DEVICE FOR RODS

CROSS-REFERENCE TO RELATED APPLICATION(S)

This application is a continuation of U.S. patent application Ser. No. 17/378,229, filed Jul. 16, 2021, which claims priority to and the benefit of U.S. Provisional Patent Application No. 63/055,100, filed Jul. 22, 2020, the contents of which are hereby incorporated by reference in their entirety, and claims priority from European Patent Application EP 20 187 183.7, filed Jul. 22, 2020, the contents of which are hereby incorporated by reference in their entirety.

BACKGROUND

Field

The application relates to a rod system including at least two rods and a connector. Further, the application relates to a connector device for connecting at least two rods. The rod system is applicable in the treatment of spinal deformities, but can also be useful in degenerative spinal surgery, for example, in dynamic stabilization or hybrid constructs.

Description of Related Art

For the treatment of early onset scoliosis of the pediatric spine, use of growing rods is known. Such growing rods may be spinal implants fixed above and below an abnormally curved portion of the spine to correct the curvature in a first step to some extent. Thereafter, the rods are prolonged in further correction surgeries to adapt them to the growth of the spine.

Rod systems including at least two rods that are connected to each other and that are used in various applications are known in the prior art.

For example, U.S. Pat. No. 9,339,307 B2 describes a bone fixation device adapted to be coupled to bone anchors that allows movement of rods to permit a screw-rod construct to lengthen in response to bone growth, without necessitating post-surgical installation adjustment of the device.

Moreover, U.S. Pat. No. 10,610,262 B2, describes a spinal distraction system including a bearing connector fastened to a fixated rod and a sliding rod, wherein the sliding rod includes a spring and a stop ring.

US 2006/0233597 describes a connection member for coupling to one or more structural rods, including a coupler body with recesses to receive the rods and a cam screw which is configured to selectively vary a size of the rod receiving recesses to impart a frictional force on the rods.

SUMMARY

It is an object of the invention to provide a rod system including at least two rods and a connector device for the rods that provide an improved or alternative way of treating various spine disorders, conditions, and/or diseases, in particular spinal deformities, and more particularly deformities in the pediatric or juvenile spine, or in degenerative spinal surgery, in particular in dynamic stabilization or hybrid construct applications.

According to an embodiment, a rod system, in particular for the spine, includes a first rod, a second rod, a connector for connecting the first rod and the second rod, the connector including a main body having a first rod seat configured to accommodate a portion of the first rod, the first rod seat having a first longitudinal axis, and a second rod seat configured to accommodate a portion of the second rod, the second rod seat having a second longitudinal axis, wherein the connector is configured to permit the first rod to be fixed to the main body and configured to permit the second rod to be selectively fixable to the main body or slidably connectable to the main body. When the second rod is slidable in the second rod seat, it can move in the axial direction of the second longitudinal axis. Also, rotation of the rod in the rod seat is possible.

The rod system may be applied in spine surgery as a correction device and/or a stabilization device.

The connector of the rod system has a low profile. This renders it particularly suitable for applications where available space is reduced or limited, such as in pediatric applications. In addition, the connector has a small width, which renders it compact and lightweight.

In a further development, the connector also includes one, preferably two, fixation members, one of which is configured to fix the first rod to the connector and the other one is configured to fix the second rod to the connector. Alternatively, the second rod can be kept sliding relative to the connector main body. In a further development, a closure member is provided which can be used instead of the fixation member when the second rod is intended to remain slidable. Thus, the rod system forms a modular system that provides various methods of use.

According to an embodiment, a connector device for connecting at least two rods includes a main body having at least a first rod seat configured to accommodate a portion of a first rod, the first rod seat having a first longitudinal axis, a second rod seat configured to accommodate a portion of a second rod, the second rod seat having a second longitudinal axis, a fixation structure configured to fix the first rod to the main body, and an orifice configured to selectively receive one of a fixation member or a closure member to either fix an inserted second rod or to close the orifice while permitting the second rod to slide.

Such a connector device has a low profile, a compact shape, and provides a modular system with a plurality of options for use.

According to a still further embodiment, a connector device for connecting at least two rods includes a main body having at least a first rod seat configured to accommodate a portion of a first rod, the first rod seat having a first longitudinal axis, a second rod seat configured to accommodate a portion of a second rod, the second rod seat having a second longitudinal axis, an orifice located between the first rod seat and the second rod seat configured to receive a fixation member, the fixation member including a screw with a head, preferably a monolithic screw with a head, wherein the head has a lower side that is configured to act on at least one of the first rod or the second rod to immobilize the first rod and/or the second rod when the first rod and/or the second rod are in the respective first and second rod seats. Preferably the lower side of the head is tapered, for example, conically tapered.

The connector device has only a few parts and has a low profile. Also, it is possible to clamp or fix the two rods simultaneously with a single fixation member. Therefore, the width of the connector device can be made small.

In a further embodiment, at least one of the first rod seat or the second rod seat, preferably both rod seats, is/are configured to selectively receive pairs of rods having different diameters, and wherein each of the pairs of rods having different diameter is fixed in the rod seat through clamping with the lower side of the fixation member at at least three contact areas.

Such a connector device is configured to connect a first pair of rods each having a first diameter or a second pair of rods each having a second diameter different from the first diameter.

In a still further embodiment, the fixation member is configured to be tilted in the orifice. Such a connector device is configured to fix two rods having different diameters simultaneously with the same fixation member.

As used in the present specification and the appended claims, the term "rod" shall be understood as including any elongate member, regardless of the cross-sectional shape. Specifically, a spinal stabilization rod as used herein, may have, for example, a substantially circular, oval, or angular cross-section. Such cross-section may vary along the length of the rod.

BRIEF DESCRIPTION OF THE DRAWINGS

Further features and advantages of the invention will become apparent from the description of embodiments by means of the accompanying drawings. In the drawings:

FIG. 14 shows a perspective view of a fixation member of the rod system of FIGS. 1 to 6.

FIG. 15 shows a side-view of the fixation member of FIG. 14.

FIG. 16 shows a closure member of the rod system of FIGS. 1 to 6.

FIG. 17 shows a side-view of the closure member of FIG. 16.

FIG. 18 shows a perspective view from a top of a sliding member of the rod system of FIGS. 1 to 6.

FIG. 19 shows a perspective view from a bottom of the sliding member of FIG. 18.

FIG. 20 shows a top view of the sliding member of FIGS. 18 and 19.

FIG. 21 shows a cross-sectional view of the sliding member of FIGS. 18 to 20, the cross-section taken along line G-G in FIG. 20.

FIG. 24 shows a perspective view from a top of a main body of a connector of the rod system of FIGS. 22 and 23.

FIG. 25 shows a perspective view from a bottom of the main body of FIG. 24.

FIG. 26 shows a front view of the main body of FIGS. 24 and 25 in a direction along a longitudinal axis of one rod seat.

FIG. 27 shows a cross-sectional view of the main body of FIGS. 24 to 26, the cross-section taken along line H-H in FIG. 26.

FIG. 28 shows a top view of the main body of FIGS. 24 to 27.

FIG. 29 shows a cross-sectional view of the main body of FIGS. 24 to 28, the cross-section taken along line I-I in FIG. 28.

FIG. 40 shows a perspective view from a top of a main body of a connector of the rod system shown in FIGS. 37 to 39.

FIG. 41 shows a perspective view from a bottom of the main body of the connector of FIG. 40.

FIG. 42 shows a top view of the main body of the connector of FIGS. 40 and 41.

FIG. 43 shows a cross-sectional view of the main body of the connector of FIGS. 40 to 42, the cross-section taken along line J-J in FIG. 42.

DETAILED DESCRIPTION

Figure 1:
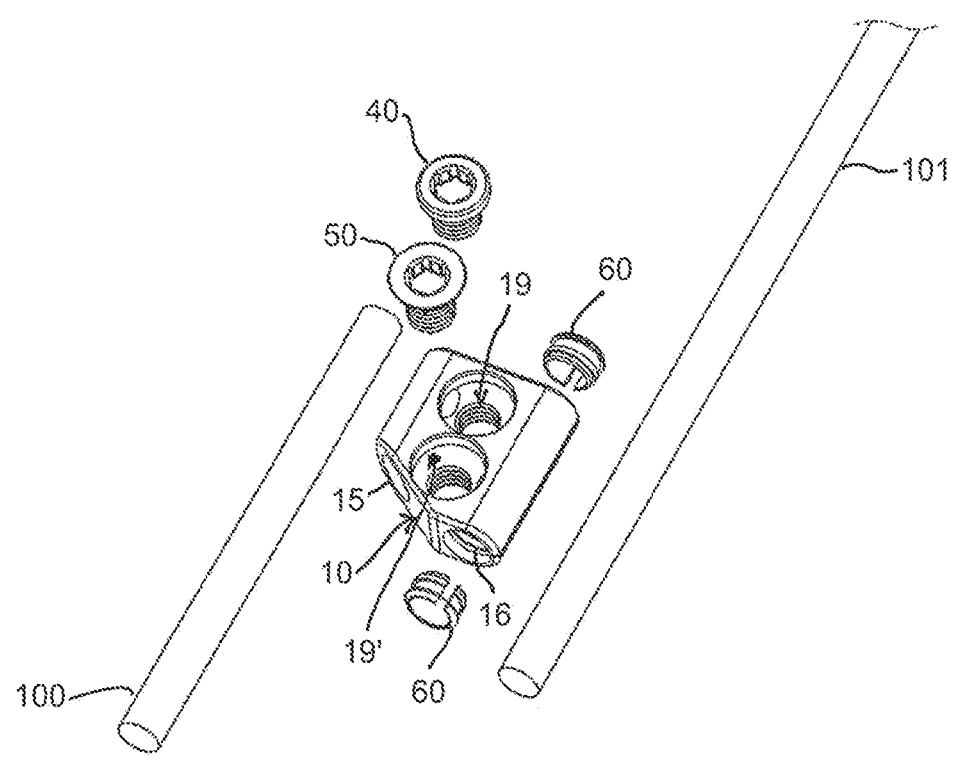
FIG. 1 shows a perspective exploded view of a rod system according to a first embodiment.
Figure 2:
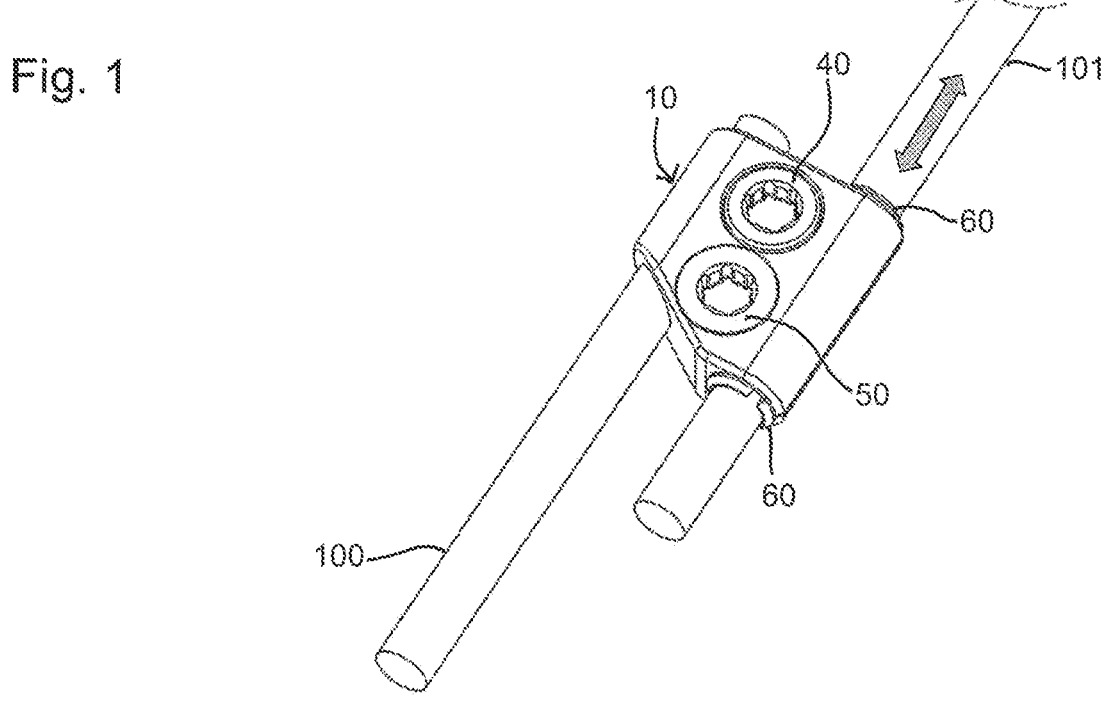
FIG. 2 shows a perspective view of the rod system of FIG. 1 in an assembled state.

Referring to FIGS. 1 and 2, a rod system according to a first embodiment includes a connector including a main body 10 and at least a first rod 100 and a second rod 101 that are intended to be connected by the connector. The rod system further includes at least one, and optionally two fixation members 40, which may be identical. One of the fixation members 40 is configured to fix the first rod 100 to the main body 10. The other one of the fixation members 40 may be used to fix the second rod 101 to the main body, if desired. Further optionally, the rod system may include a closure member 50 that is configured to close an orifice in the main body 10 when the second rod 101 is intended to remain slidable. Sliding members 60 may also be part of the rod system that facilitate sliding of the second rod 101 in the main body 10.

The first rod 100 and the second rod 101 may be substantially identical. They may have a circular cross-section and preferably a smooth surface. However, the rods are not limited to such a design. Usually, the first rod 100 and the second rod 101 are configured to be connected to bone anchors (not shown). Such bone anchors could be, for example, pedicle screws that are inserted into the pedicles of vertebrae.

The first rod 100 is configured to be connected to the main body 10 in such a manner that the rod is fixed, or in other words immobilized, with respect to the main body 10 by using the fixation member 40. The second rod 101 can remain movable, specifically slidable, with respect to the main body 10, for example within the sliding members 60. The second rod 101 may alternatively be immobilized using a second fixation member 40. Hence, the second rod 101 may be kept slidable or may be fixed depending on a particular desired application. If second rod 101 remains slidable, the closure member 50 may be used to close the respective orifice.

Figures 3, 4, 5, 6:
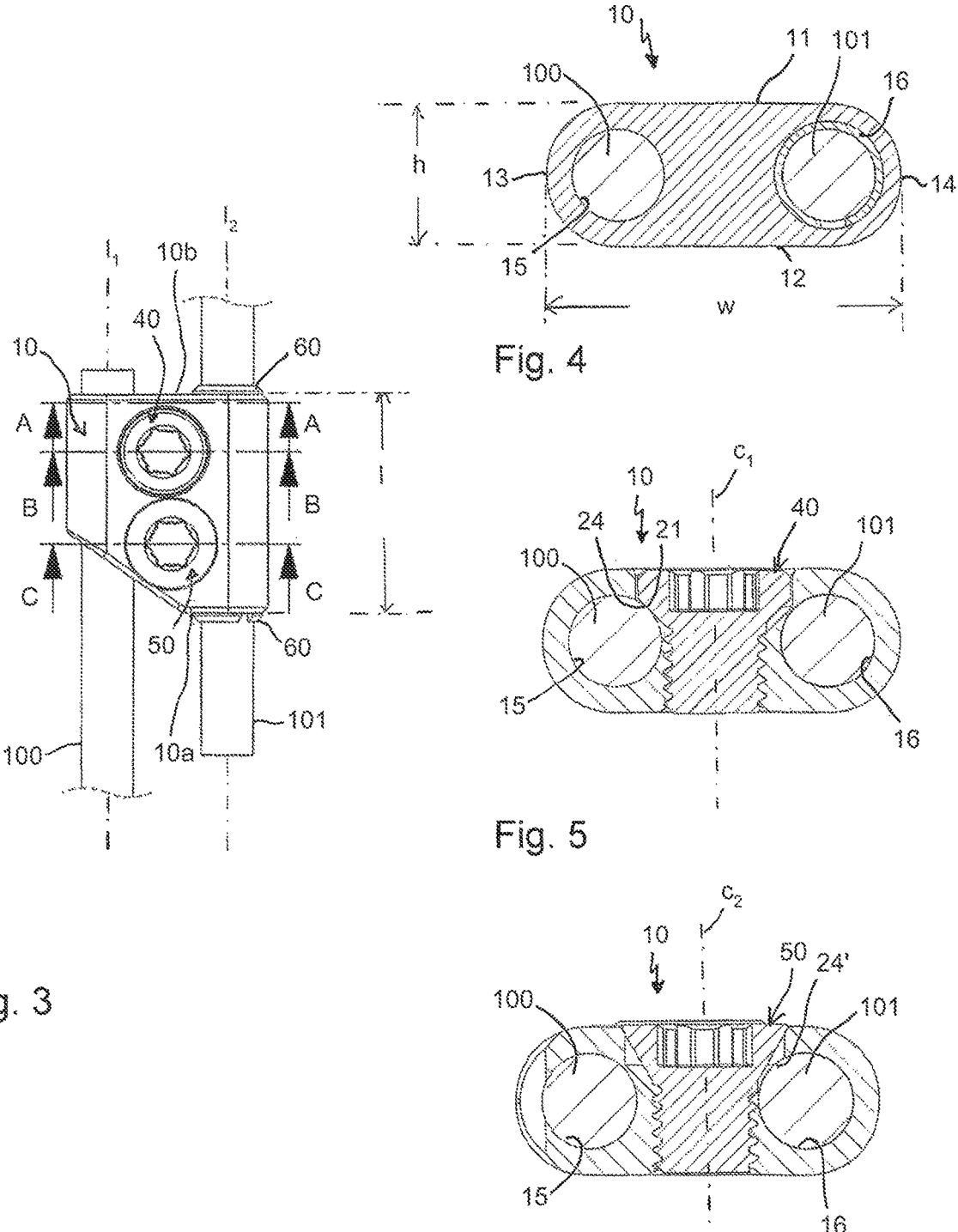
FIG. 3 shows a top view of the rod system of FIGS. 1 and 2.
FIG. 4 shows a cross-sectional view of the rod system of FIGS. 1 to 3, the cross-section taken along line A-A in FIG. 3.
FIG. 5 shows a cross-sectional view of the rod system of FIGS. 1 to 3, the cross-section taken along line B-B in FIG. 3.
FIG. 6 shows a cross-sectional view of the rod system of FIGS. 1 to 3, the cross-section taken along line C-C in FIG. 3.
Figure 7:
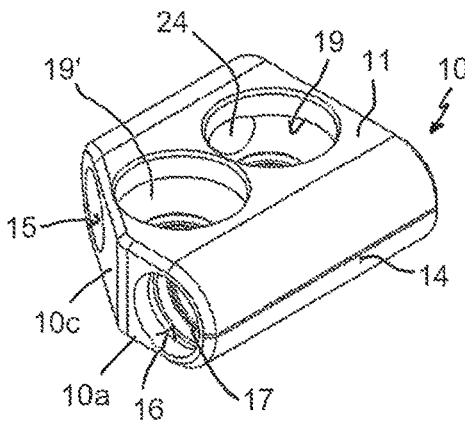
FIG. 7 shows a perspective view from a top of a main body of a connector of the rod system of FIGS. 1 to 6.
Figure 8:
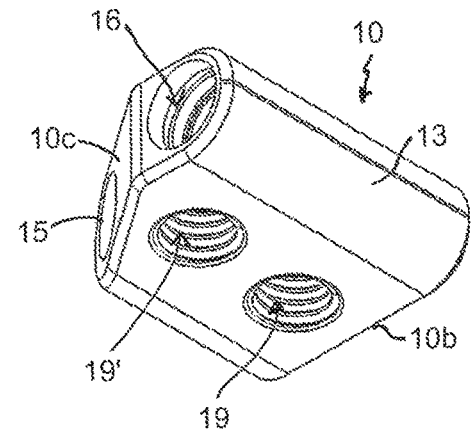
FIG. 8 shows a perspective view from a bottom of the main body of FIG. 7.
Figure 9:
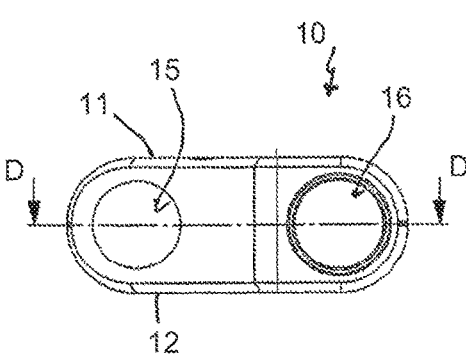
FIG. 9 shows a front view of the main body of FIGS. 7 and 8 in a direction of a longitudinal axis of one rod seat.

Referring in addition to FIGS. 3 to 13, the main body 10 will be described in greater detail. The main body 10 is preferably a monolithic part that has a substantially flat top 11 and a substantially flat bottom 12 that are substantially parallel to each other and that define a height h of the main body 10. The top 11 and the bottom 12 are connected via, for example, outwardly bulged cylindrical sides 13, 14, the distance between the outermost portions of which define a width w of the main body 10, as shown in detail in FIG. 4. The main body 10 further has a front end 10a and a rear end 10b in a top view, as shown in FIG. 3, a distance between which defines a length l of the main body. By the height h, the width w, and the length l, a height direction, a width direction, and a length direction, respectively, are defined.

At a distance from each of the sides 13 and 14, there are a first rod seat 15 and a second rod seat 16, respectively, that each extend from the front end 10a to the rear end 10b completely through the main body 10. The first rod seat 15 is configured to receive the first rod 100 and the second rod seat 16 is configured to receive the second rod 101. More specifically, the first rod seat 15 is formed as a cylindrical channel with an inner diameter that substantially matches an outer diameter of the first rod 100 so that the first rod 100 fits therein, for example with friction. The first rod seat 15 defines a first longitudinal axis $I_1$ which may be located at the center of the main body 10 in the height direction. The second rod seat 16 is also a cylindrical channel defining a second longitudinal axis $I_2$ which may also be located at the center of the main body in the height direction. A central portion of the second rod seat 16 has an inner diameter that substantially matches an outer diameter of the second rod 101 so that the second rod 101 fits therein. Adjacent to the front end 10a and adjacent to the rear end 10b, the second rod seat 16 has receiving sections 17 with a slightly greater inner diameter than the central portion of the rod seat for receiving the sliding members 60, respectively. Circumferential inner grooves 18 are formed in the receiving sections at a distance from the front end 10a and the rear end 10b, respectively, appropriate for receiving a corresponding projection of the sliding member 60. Thereby, it can be ensured that the sliding members 60, once inserted, are held in the receiving sections 17 and are prevented from falling out of the second the rod seat 16.

The longitudinal axis $I_1$ of the first rod seat 15 and the longitudinal axis $I_2$ of the second rod seat 16 are arranged parallel to each other and at the same height with respect to the top 11 and/or the bottom 12. As can be seen in the figures, the rod seats 15, 16 are substantially closed around an inserted rod. Thus, an inserted rod is circumferentially encompassed by the rod seat at least over a certain length except at positions where the fixation member 40 acts onto the rod.

Between the first rod seat 15 and the second rod seat 16, a first orifice 19 and a second orifice 19' are formed that serve for selectively receiving the fixation member 40 or the closure member 50. The first orifice 19 defines a central axis $c_1$ as shown in FIG. 5 that extends perpendicular to the first longitudinal axis $I_1$ of the first rod seat 15 and perpendicular to the second longitudinal axis $I_2$ of the second rod seat 16. The first central axis $c_1$ of the first orifice 19 is located at a distance from the rear end 10b that is smaller than the distance between $c_1$ and the front end 10a. Moreover, the first central axis $c_1$ is closer to the first rod seat 15 than to the second rod seat 16 in the width direction.

Figure 12:
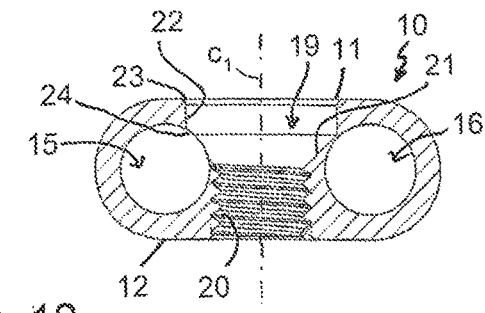
FIG. 12 shows a cross-sectional view of the main body of FIGS. 7 to 11, the cross-section taken along line E-E in FIG. 11.

The first orifice 19 extends completely from the top 11 to the bottom 12. Adjacent to the bottom 12, the orifice 19 includes a threaded bore 20 for receiving a shaft of the fixation member 40 and adjacent to the top 11, the orifice 19 has an enlarged space for receiving a head of the fixation member 40 in a countersink manner. The enlarged space has, adjacent to the threaded bore 20, a tapered portion 21 that tapers towards the threaded bore 20, and following the tapered portion 21, a substantially cylindrical portion 22 which opens, preferably with a small bevel 23, to the top 11. The tapered portion 21 and the cylindrical portion 22 intersect the first rod seat 15 at the side facing the first rod seat 15, such that a cutout 24 is formed that provides an opening between the first orifice 19 and the first rod seat 15. Referring to FIGS. 5 and 12 in particular, the cutout 24 is located above the center of the main body 10 in the height direction, so that the fixation member 40 can press from a position above the middle of the first rod 100 when the first rod 100 is inserted into the first rod seat 15. On the opposite side of the cutout 24 in the width direction, the tapered portion 21 of the orifice 19 is spaced apart from the second rod seat 16, so that an inserted fixation member does not contact a second rod 101 inserted into the second rod seat 16.

Figure 10:
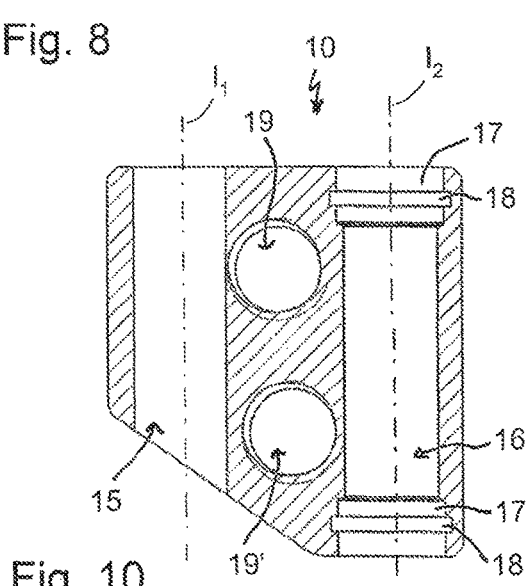
FIG. 10 shows a cross-sectional view of the main body of FIGS. 7 to 9, the cross-section taken along line D-D in FIG. 9.
Figure 11:
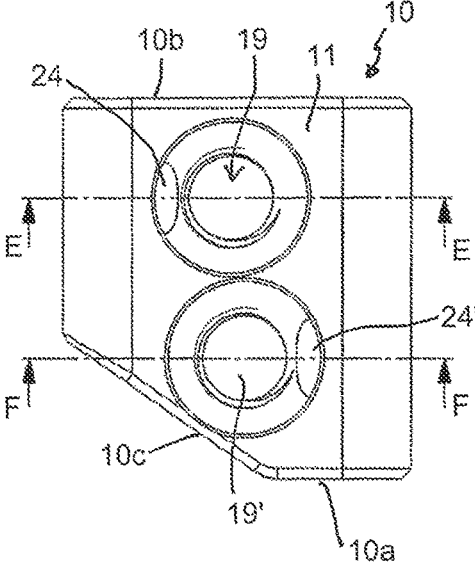
FIG. 11 shows a top view of the main body of FIGS. 7 to 10.
Figure 13:
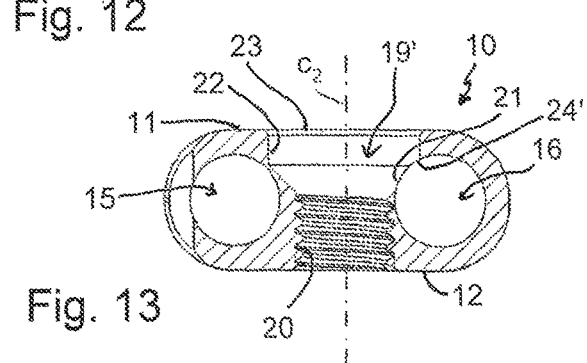
FIG. 13 shows a cross-sectional view of the main body of FIGS. 7 to 11, the cross-section taken along line F-F in FIG. 11.
Figures 22, 23:
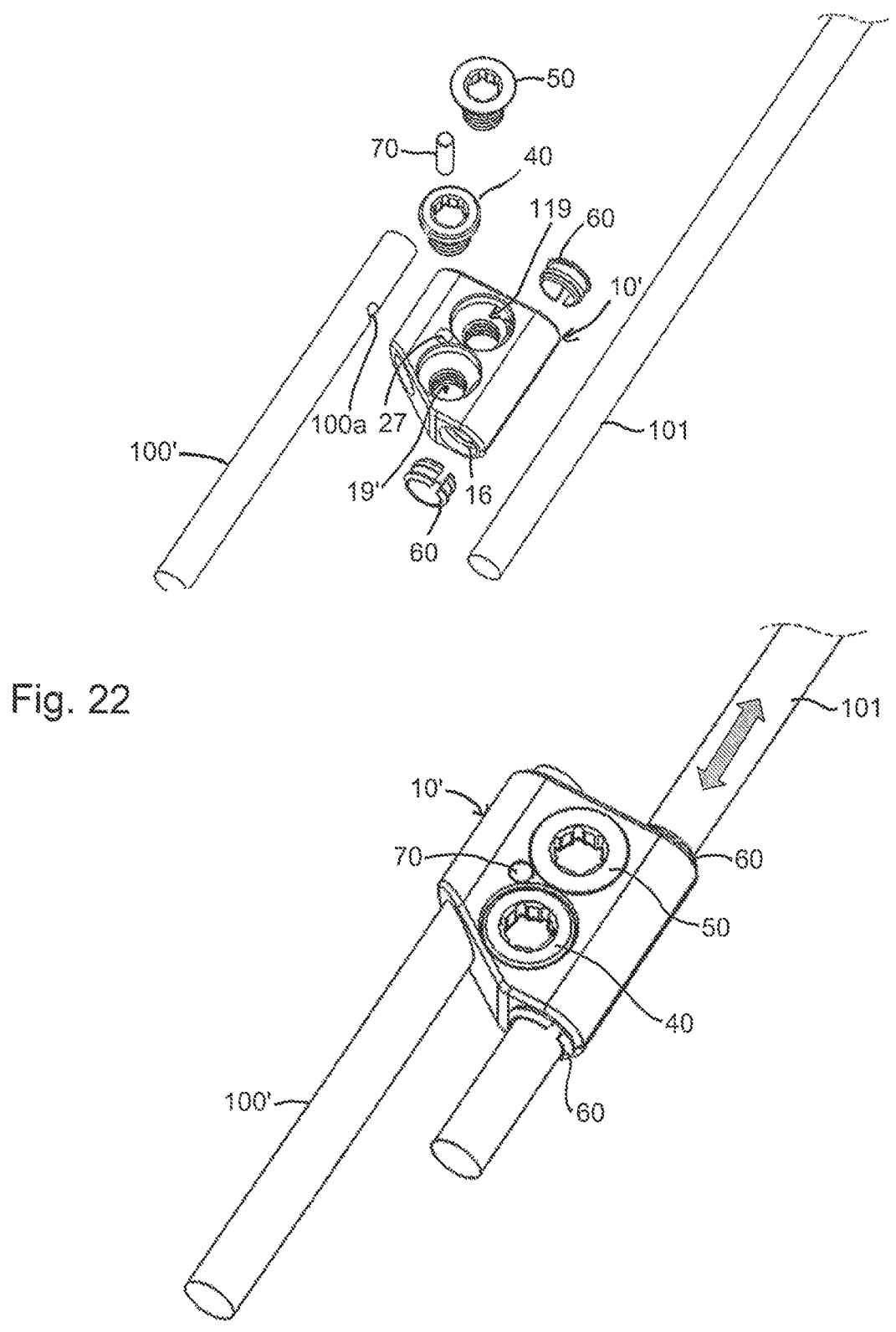
FIG. 22 shows a perspective exploded view of a rod system according to a second embodiment.
FIG. 23 shows a perspective view of the rod system of FIG. 22 in an assembled state.

Referring now in greater detail to FIGS. 3 and 10, the second orifice 19' extends completely from the top 11 to the bottom 12 of the main body 10 and defines a second central axis $c_2$. The second central axis $c_2$ of the second orifice 19' extends perpendicular to the second longitudinal axis $I_2$ of the second rod seat 16 and also perpendicular to the first longitudinal axis $I_1$ of the first rod seat 15. The second orifice 19' is closer to the front end 10a than to the rear end 10b of the main body 10. Moreover, the second orifice 19' is closer to the second rod seat 16 in the width direction than it is to the first orifice. As a result, the central axes $c_1$, $c_2$ of the first and the second orifice 19, 19', respectively, are offset in the width direction. Similar to the first orifice 19, the second orifice 19' includes a threaded bore 20 adjacent to the bottom 12 and an upper portion that has the cylindrical portion 22 adjacent to the top 11 and an intermediate tapered portion 21 sandwiched between them. The second orifice 19' is close to the second rod seat 16, such that the tapered portion 21 and the cylindrical portion 22 intersect the second rod seat 16, thereby forming a cutout 24' or opening between the second orifice 19' and the second rod seat 16, as best seen in FIGS. 11 and 13. By means of the cutout 24', a tapered portion 43 of the fixation member 40 is permitted to contact the second rod 101 when the second rod 101 is in the second rod seat 16. The tapered portion 21 is above the second longitudinal axis $I_2$ of the second rod seat 16. Hence, an inserted fixation member 40 is configured to press from an upper side of the second rod 101 on the second rod 101. At the opposite side of the cutout 24' in the width direction, the second orifice 19' is spaced apart from the first rod seat 15, so that an inserted fixation member 40 cannot act onto the first rod 100.

Lastly, the front end 10a of the main body 10 includes a slanted portion 10c that may extend from a distance from the opening formed by the second rod seat 16 in the front end 10a to approximately a short distance behind or past the second central axis $c_2$ of the second orifice 19' in the length direction of the main body 10, as depicted in FIG. 11. By means of the slanted surface 10c, material can be saved and the connector can be made more compact.

The main body has a low profile, since above and beneath the first rod seat 15 and the second rod seat 16, only a minimum of necessary material is present. Also, because the fixation members are placed into the orifices which are arranged one after the other in the length direction, while the action zones 24, 24' of the fixation members 40 with the first rod 100 and the second rod 101 have only a minimum necessary distance in the width direction, the main body is very slim in the width direction. Finally, by means of the slanted portion 10c at the front end 10a, the main body can be constructed more lightweight.

Referring now in addition to FIGS. 14 and 15, the fixation member 40 will be described. The fixation member 40 is in the form of a screw having a threaded shaft 41 and a head 42. The threaded shaft 41 is configured to cooperate with the threaded hole 20 of the first orifice 19 and the second orifice 19', respectively. The head 42 has a shape that generally matches the shape of the upper portion of the first orifice 19 and the second orifice 19', respectively. More specifically, the head 42 includes a tapered portion 43 adjacent the threaded shaft 41 that is configured to fit into the tapered portion 21 of the first and second orifice 19, 19', respectively, and a cylindrical portion 44 adjacent the tapered portion 43 that is configured to fit into the cylindrical portion 22 of the first and second orifice 19, 19', respectively. A beveled portion 45 may be provided that is between the cylindrical portion 44 and a free end surface 42a of the head 42. In the free end surface 42a, a tool engagement recess 46 may be formed. Various shapes of tool engagement recesses may be conceivable, such as a polygon recess, a torx-shaped recess, any type of longitudinal grooves, or any other engagement structure. A length of the fixation member 40 along its screw axis is such that the head 42 of the fixation member can be fully immersed or countersunk into the upper portion of the first and second orifice 19, 19', respectively, and that preferably the threaded shaft 41 does not protrude substantially out of the threaded bore 20. This further contributes to the low profile of the connector.

As shown in FIG. 5, when the fixation member is inserted into the first orifice 19, the tapered portion 43, which is preferably a conically-tapered portion, is permitted to contact the first rod 100 from an upper side thereof, i.e. from a side above the middle of the rod, when the first rod 100 is in the first rod seat 15. Tightening the fixation member 40 increases the pressure onto the first rod 100, so that the first rod 100 is immobilized in the first rod seat 15. Similarly, when the fixation member 40 is inserted into the second orifice 19', it can be fully immersed or countersunk therein, so that neither the head 42 nor the threaded shaft 41 protrude out of the top 11 or the bottom 12, respectively. The tapered portion 43 is configured to contact the second rod 101 through the cutout 24'. Tightening the fixation member 40 in the threaded bore results in an increasing pressure onto the second rod 101 until the second rod 101 is immobilized or fixed in the second rod seat 16.

Referring now to FIGS. 16 and 17, the optionally provided closure member 50 is in the form of a screw having a threaded shank 51 that is configured to cooperate with the threaded bore 20 in the first and second orifice 19, 19', respectively, and a head 52. The head 52 has a length in the axial direction of the screw such that the head can axially fit or be immersed into the upper portion of the first and second orifice 19, 19', respectively, as can be seen in particular in FIG. 6. The head 52 is tapered between the shaft 51 and substantially the free end surface 52a, wherein the taper may be steeper than that of the tapered portion 43 of the fixation member 40. By means of this, the head 52 can be prevented from extending through the cutout 24, 24' of the first or second orifice 19, 19' and therefore prevented from contacting the first or second rod. A small bevel 53 adjacent the free end surface may also be formed. A length of the closure member 50 is such that the closure member can be immersed in the second orifice 19' without portions extending out of the top 11 or the bottom 12. In the free end surface 52a of the head 52, a tool engagement recess 54 is cut out that may have any suitable tool engagement shape, such as a polygon, a torx-shape, or any longitudinal grooves or other suitable shape.

Referring now in greater detail to FIGS. 18 to 21, the sliding members 60 are preferably identical parts. Each sliding member 60 is formed as a sleeve with a first end 60a, a second end 60b, and a longitudinal slot 61 extending from the first end to the second end. By means of the slot 61, the sliding member 60 is compressible such that it can be inserted into the receiving section 17 of the second rod seat 16. In the compressed configuration, an inner diameter of the sliding member 60 is only slightly greater than an outer diameter of the second rod 101 such that the second rod 101 can slide within the sliding member 60. An outer base diameter of the sliding member 60 corresponds to an inner diameter of the receiving section 17 when the sliding member is inserted therein. At a distance from the second end 60b, a circumferential protrusion 62 is provided that fits into the groove 18 of the receiving section. By means of this, the sliding member 60 is axially fixed in the receiving section 17. Adjacent the first end 60*a*, a circumferential protrusion 63 is formed that tapers and narrows towards the first end 60*a*. The circumferential protrusion 63 extends out of the second rod seat 16 at the front end 10*a* or the rear end 10*b* of the main body 10 once the sliding member is in the receiving section 17. Thereby, further insertion of the sliding member into the second rod seat 16 is also prevented. The sliding members 60 are assembled with the main body 10 in such a manner that they are inserted into the second rod seat 16 with their second end 60*b* being the leading end.

The main body, the first and second rods, the fixation member or fixation members, and the closure member are made of a bio-compatible material, such as a bio-compatible metal or a metal alloy, or of a bio-compatible plastic material. Suitable materials may be titanium or stainless steel, NiTi alloys, for example Nitinol, or plastics like polyether ether ketone (PEEK) or poly-L-lactide acid (PLLA). The parts may be made of the same or of different materials from one another.

The sliding members may be specifically made of a plastic material that facilitates sliding, such as PEEK or polyurethane. The sliding members may also be made of the same material as the other components of the rod system, and can be coated with a coating that facilitates sliding of the second rod therein.

In use, the rod system is connected with bone anchors, for example, two bone anchors that are inserted in vertebrae, for example, of different motion segments of the spine such that the rod system bridges the respective motion segments. The bone anchors may be, for example, monoaxial or polyaxial pedicle screws inserted into the pedicles of vertebrae. In greater detail, the first rod 100 may be connected to a first bone anchor at the side of the front end 10*a*, and the second rod 101 may be connected to a second bone anchor at the side of the rear end 10*b* of the main body 10. The first rod 100 may be connected to the main body 10 in a way such that only a small portion of the first rod projects out of the rear end 10*b* of the main body 10. Once fixed to the bone anchor, the first rod is immobilized relative to the main body 10 by inserting the fixation member 40 into the first hole 19 and tightening the fixation member. Thereby, the slanted portion 43 of the head 42 of the fixation member presses through the cutout 24 onto the first rod 100 to fix the same.

It shall be noted, that by means of adjusting the strength of tightening of the fixation member 40, the frictional force holding the rod can be adjusted. For example, for the purpose of correction steps, a friction hold that can be manually overcome may be sufficient, whereas for final fixation the fixation member can be fully tightened.

The second rod 101 may be connected to the second bone anchor while remaining slidable with respect to the main body 10. Due to the sliding members, the sliding is considerably facilitated. Hence, the second rod 101 allows the distance between the first and the second bone anchor to continuously vary corresponding to the sliding of the second rod with respect to the main body, and therefore, with respect to the fixed first rod 100. In the second orifice 19', the closure member 50 may be inserted to close the orifice so that the orifice can be maintained substantially free from vessels or tissue growing into it. Alternatively, instead of closing the second orifice 19' with the closure member 50, another fixation member 40 can be inserted into the second orifice 19' to clamp and fix the second rod 101 at a desired axial position with respect to the main body 10. When tightening the fixation member 40, the tapered portion 43 presses through the cutout 24' onto the second rod 101 until the second rod is immobilized.

In various examples of use, a surgeon can selectively use either another fixation member 40 to fix the second rod 101 or a closure member 50 to close the second orifice 19'. Keeping the second rod 101 slidable, the rod system can be used, for example, as a growing rod system. It shall be noted that alternatively, the second rod 101 can be fixed and the first rod 100 can be kept slidable or, alternatively both rods can be kept slidable. It may be advantageous to provide a stop at the sliding rod to prevent the sliding rod from falling out. Such a stop may be, for example, a clamping ring around the free end of the sliding rod which is close to the main body.

Thus, the stabilization system provides a modular system that permits a multitude of applications with sliding and/or fixed rods.

Referring now to FIGS. 22 to 29, a second embodiment of the rod system will be described. Parts and portions that are the same or similar to those of the first embodiment will be marked with the same reference numerals, and the descriptions thereof will not be repeated. The rod system according to the second embodiment differs from the rod system of the first embodiment mainly in that the first rod is permanently fixed to the main body of the connector using a pin 70. Functionally corresponding to the first orifice in the first embodiment, a pin hole 27 for receiving the pin extends from the top 11 completely to the bottom 12 and is arranged offset from the middle of the main body 10' in the width direction towards the first rod seat 15. The pin hole 27 has a size and is positioned at a position such that the pin hole intersects the first rod seat 15, as shown in particular in FIG. 27. In the length direction, the pin hole 27 is formed approximately at the center of the main body 10'. A central axis of the pin hole 27 extends perpendicular to the first longitudinal axis $I_1$ of the first rod seat 15.

The first rod 100' includes a substantially cylindrical recessed portion 100*a* that is at an axial position corresponding to the pin hole when the first rod 100' is inserted into the first rod seat and projects only slightly out of the rear end 10*b*. The pin 70 forms a first fixation member that is configured to be inserted into the pin hole 70, thereby engaging the recessed portion 100*a* of the first rod 100' when the first rod 100' is in the first rod seat 15.

A third orifice 119 is formed in the main body 10' between the second orifice 19' and the rear end 10*b*. The third orifice 119 has a central axis that is perpendicular to the longitudinal axes $I_1$ and $I_2$ of the first and second rod seats 15, 16 and positioned in the width direction at the same position as the central axis $c_2$ of the second orifice 19'. The third orifice 119 is identical in shape to the second orifice 19'. Hence, there is a cutout 124 forming an opening between the third orifice 119 and the second rod seat 16. The pin hole 27 may be arranged in the middle between the second orifice 19' and the third orifice 119 on the side facing towards the first rod seat 15.

In the rod system of the second embodiment, the first rod 100' is fixed to the main body 10' in a specific axial position. The fixation is effected by the pin 70 engaging the recess 100*a* of the first rod 100'. As the pin may be press-fit into the pin hole 27, the axial and rotational fixation of the first rod 100' is permanent during ordinary use of the rod system. Moreover, the rod 100 can also be welded to the main body 10', so that the connection is non releasable.

In use, two fixation members 40 can be placed into the second and third orifice 19', 119, respectively, so that an enhanced fixation can be achieved by using two fixation members. Alternatively, one fixation member 40 and one closure member 50 may be used or two closure members 50 may be used for the second and third orifices 19', 119 to keep the second rod 16 slidable. It shall be noted that the orifices 19', 119 can also remain open, i.e. without inserting a closure member 50.

In a modified embodiment, the first rod 100 and the main body 10' can be a monolithic part. They may be, for example, machined out of one piece of material. In this modified embodiment, the pin is not needed.

Figure 30:
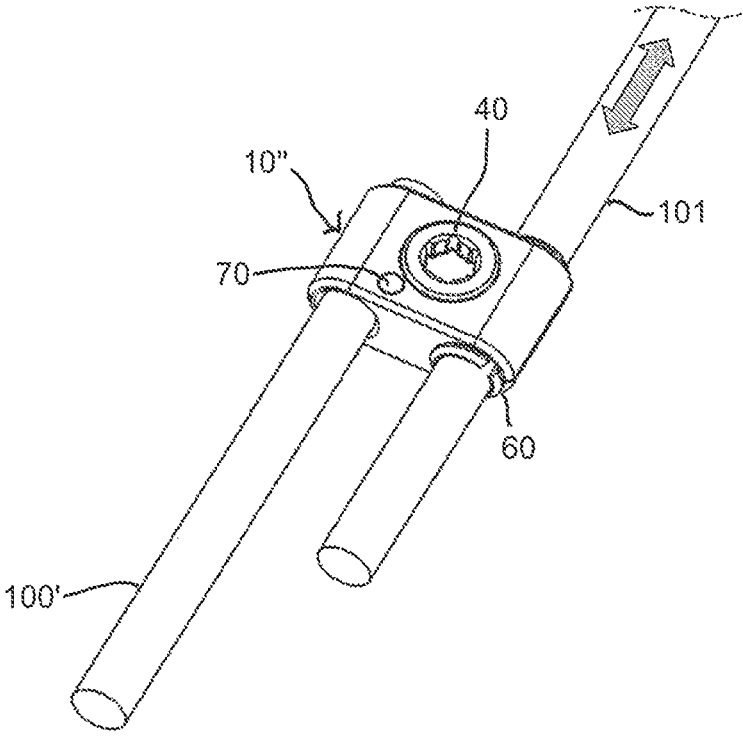
FIG. 30 shows a perspective view of a rod system according to a third embodiment in an assembled state.

Referring to FIG. 30, a third embodiment of the rod system will be described. Parts and portions that are identical or similar to those of the first or second embodiments are indicated with the same reference numerals, and the descriptions thereof will not be repeated. the first rod 100' is identical to that of the second embodiment, i.e. the first rod has the recess 100a for engagement with the pin 70. The main body 10'' lacks the third orifice 119 of the second embodiment. As a result, the main body 10'' only has the pin hole 27 for engagement with the pin 70 and one orifice 119 for receiving a fixation member 40 or a closure member 50. The front end 10a lacks the slanted portion 10c so that the front end 10a is substantially parallel to the rear end 10b over the whole width. The first rod 100' is fixed to the main body 10'' via the pin 70 which is press-fit into the pin hole 27. Optionally, the first rod 100' can be welded to the main body 10''. The second rod 101 can be fixed via fixation member 40 or can slide in the second rod seat 16.

The rod system according to the third embodiment has an even more reduced size in the length direction. In a modified embodiment, the first rod 100' and the main body 10'' can also be a monolithic part, so that the pin is not needed.

Figures 31, 32:
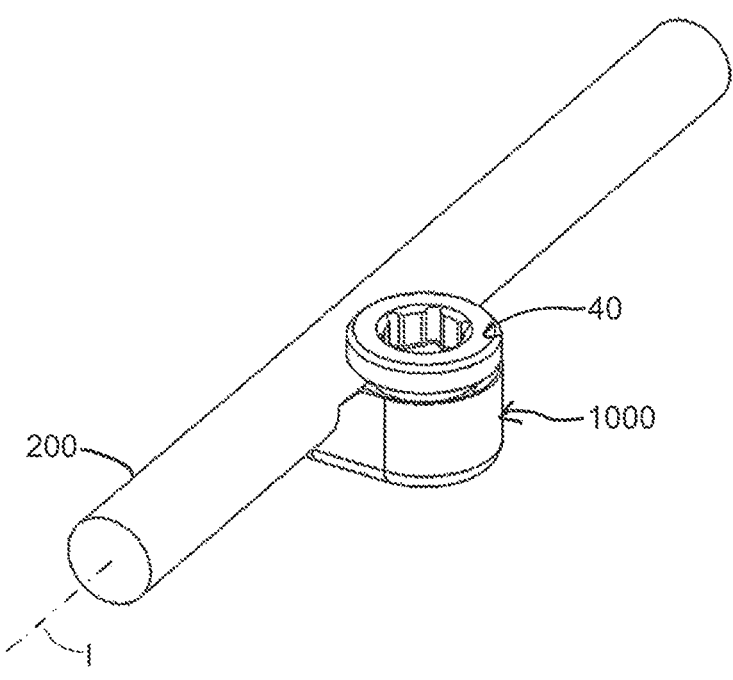
FIG. 31 shows a perspective view of a rod system including only one rod according to a further embodiment.
FIG. 32 shows a cross-sectional view of the rod system of FIG. 31, the cross-section taken in a plane perpendicular to a longitudinal axis of the rod and extending through a center of a fixation member.

Referring to FIGS. 31 and 32, a still further embodiment of a rod system will be described. The rod system includes a rod 200 which may be identical to the rod 100 or 101 of the previous embodiments, and a connector including a main body 1000 and a fixation member 40. The main body 1000 is a body with a top 11', a bottom 12', and sides 13', 14', wherein the sides may have a substantially cylindrical outer surface. It shall be noted, however, that the overall shape of the main body can be any shape, for example, cuboid. In the top 11', a single rod seat 150 is formed which is substantially cylinder segment-shaped for a circular rod 200. The rod seat is open, such that the circular rod can be inserted from the top 11'. Laterally offset from the rod seat 150, an orifice 190 is formed, a central axis c of which extends perpendicular to the longitudinal axis l of the rod seat 150. The orifice 190 has a threaded hole 191 that is configured to receive the threaded shaft 41 of the fixation member 40. On the side facing away from the rod seat, the orifice 190 may have a tapered portion 192 for receiving the tapered portion 43 of the fixation member 40. On the opposite side, the inserted rod is accessible by the head of the fixation member 40. More specifically, the orifice 190 is at a position such that, when the fixation member 40 is inserted into the orifice 190 and tightened, the tapered portion 43 of the head 42 of the fixation member 40 contacts the rod 200 from above and presses the rod 200 into the rod seat 150. As a result, the rod 200 is fixed or immobilized only by tightening the fixation member. The rod system includes only a few parts of simple structure. Moreover, the connector has a very low profile.

Figure 33:
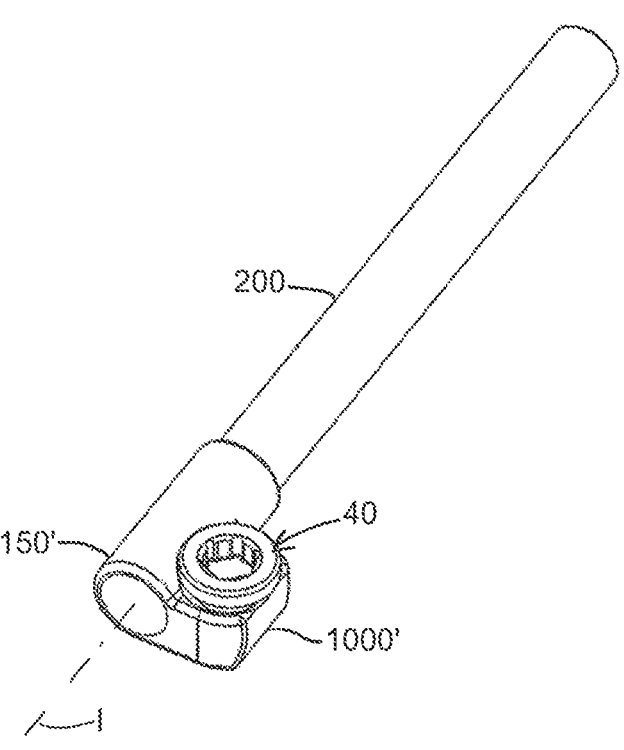
FIG. 33 shows a perspective view of another embodiment of a rod system including only one rod.
Figure 34:
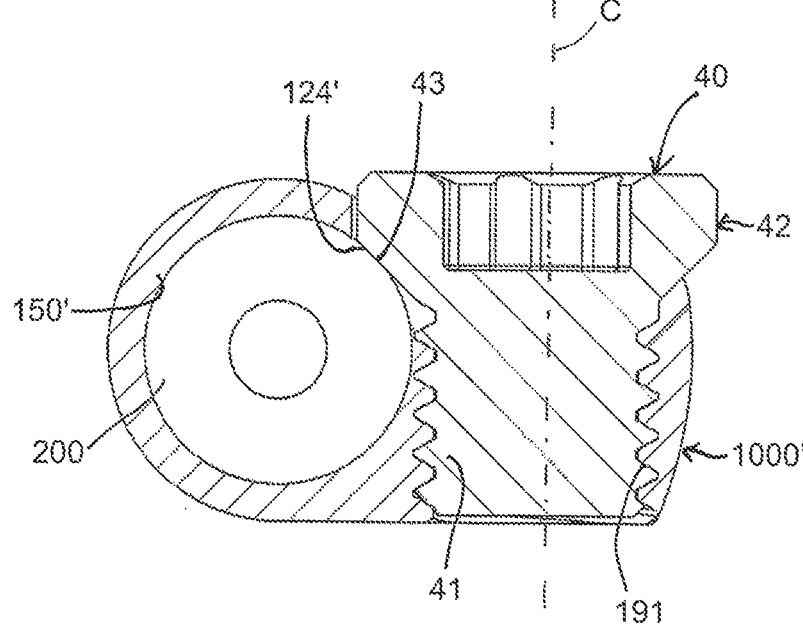
FIG. 34 shows a cross-sectional view of the rod system of FIG. 33, the cross-section taken in a plane perpendicular to a longitudinal axis of the rod and extending through a center of a fixation member.

Referring to FIGS. 33 to 34, a still further embodiment of a rod system is shown. The rod system differs from the rod system in FIGS. 31 and 32 mainly in that the main body 1000' includes a rod seat in the form of a sleeve-like portion 150' that may have a sleeve-like prolongation or extension 200 with a smaller outer diameter. The two portions 150' and

200 form a rod extension in which a further rod (not shown) can be inserted. Hence the rod seat is substantially closed around an inserted rod. An outer contour of the main body 1000' in the portion around the orifice 190 may be substantially rectangular, with one side attached to the sleeve-like portion forming the rod seat 150'. The upper portion of the orifice 190 intersects the rod seat portion 150' such that a cutout 124' forms an opening that permits the tapered portion 43 of the head 42 of the fixation member 40 to press on an upper portion of an inserted rod. A free end surface in the axial direction of the rod seat portion 150' may be open or closed. In use, tightening the fixation member 40 against an inserted rod clamps and finally fixes the rod in the axial position.

Figure 35:
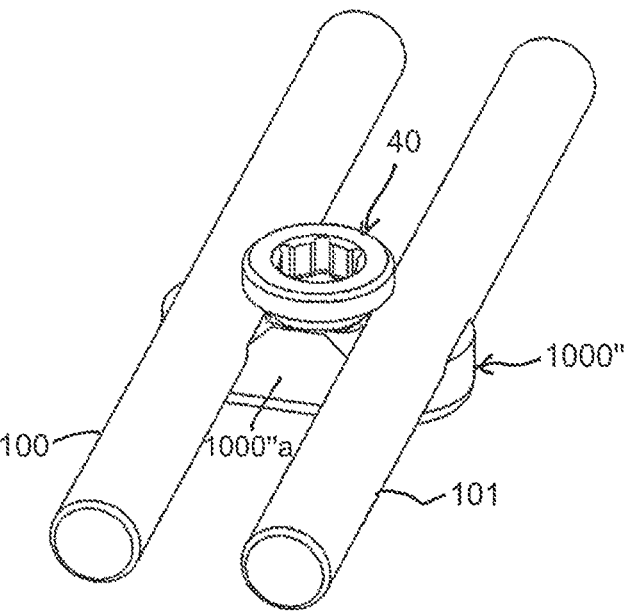
FIG. 35 shows a perspective view of a still further embodiment of a rod system.
Figure 36:
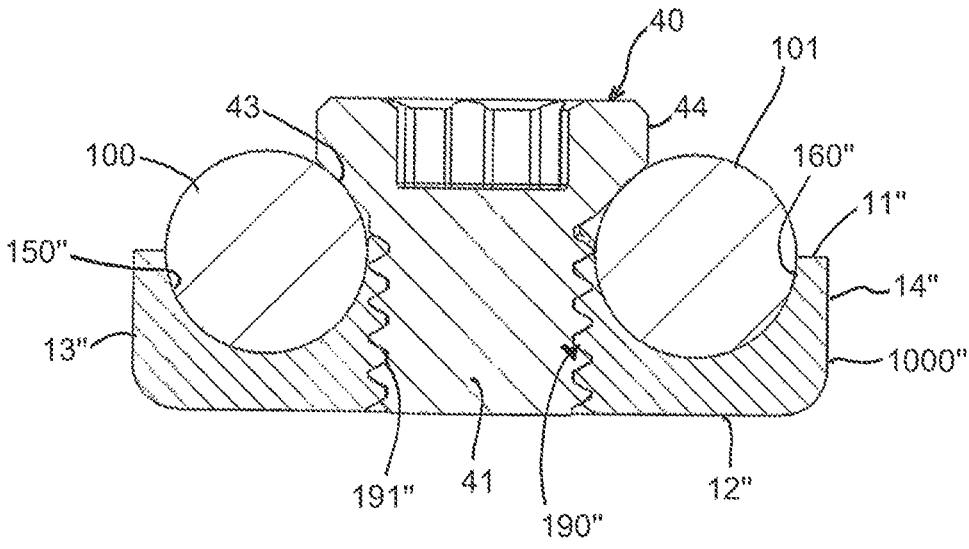
FIG. 36 shows a cross-sectional view of the rod system of FIG. 35, the cross-section taken in a plane perpendicular to longitudinal axes of two inserted rods and extending through a center of a fixation member.
Figure 37:
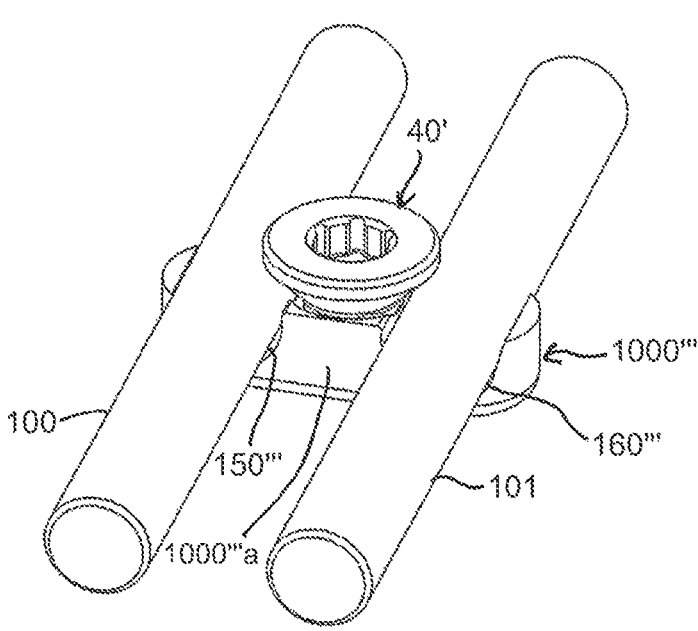
FIG. 37 shows a perspective view of a still further embodiment of a rod system in an assembled state.

Referring to FIGS. 35 and 36, a still further embodiment of a rod system includes two rods 100, 101 having a same diameter, a main body 1000'', and a fixation member 40. The main body 1000'' has a top 11'', an opposite bottom 12'' which are substantially parallel, two outwardly bulged cylinder segment-shaped sides 13'', 14'' joining the top 11'' and the bottom 12'', a front end 1000''a, and a rear end (not visible in the Figures). In the top 11'', two cylinder segment-shaped rod seats 150'', 160'' are formed having longitudinal axes $I_1$ and $I_2$, respectively, that are substantially parallel to each other. The rod seats 150'', 160'' are open so that the rods can be inserted from the top 11''. In the center of the main body between the rod seat 150'', 160'', an orifice 190'' is formed that has a threaded hole 191''. A length of the threaded hole 191'' is such that, when the fixation member 40 is inserted with the threaded shaft 41, the fixation member can be tightened to press with the tapered portion 43 onto an upper side of the rods 100, 101 which are inserted into the first and second rod seats 150'', 160''. With the fixation member 40, both rods can be fixed simultaneously. The rod system has few parts, a simple structure, and a low profile.

Figure 38:
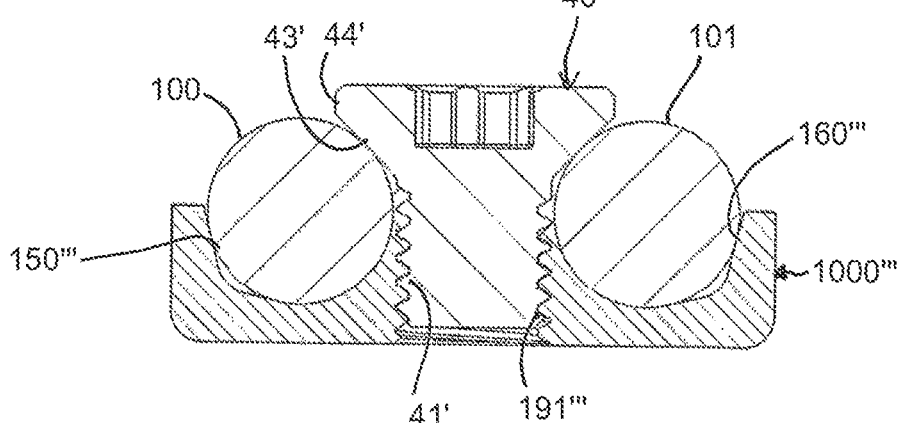
FIG. 38 shows a cross-sectional view of the rod system of FIG. 37, the cross-section taken in a plane perpendicular to longitudinal axes of two inserted rods and extending through a center of a fixation member, wherein the rods each have a first diameter.
Figure 39:
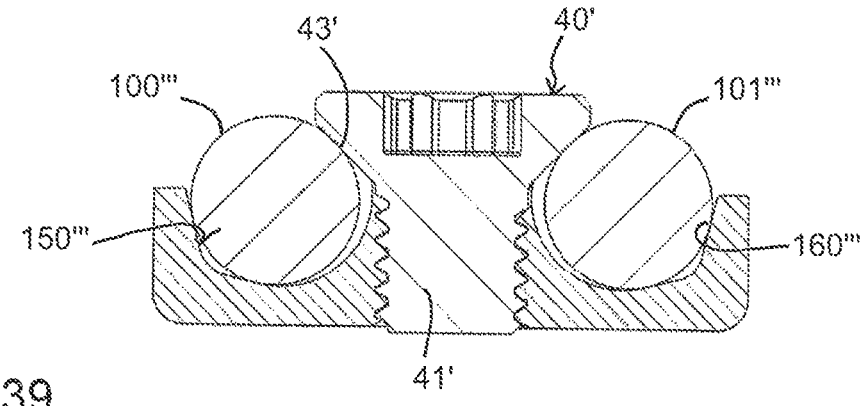
FIG. 39 shows a cross-sectional view of the rod system of FIG. 37, with two inserted rods each having a second diameter that is smaller than the first diameter of the rods shown in FIG. 38.
Figure 44:
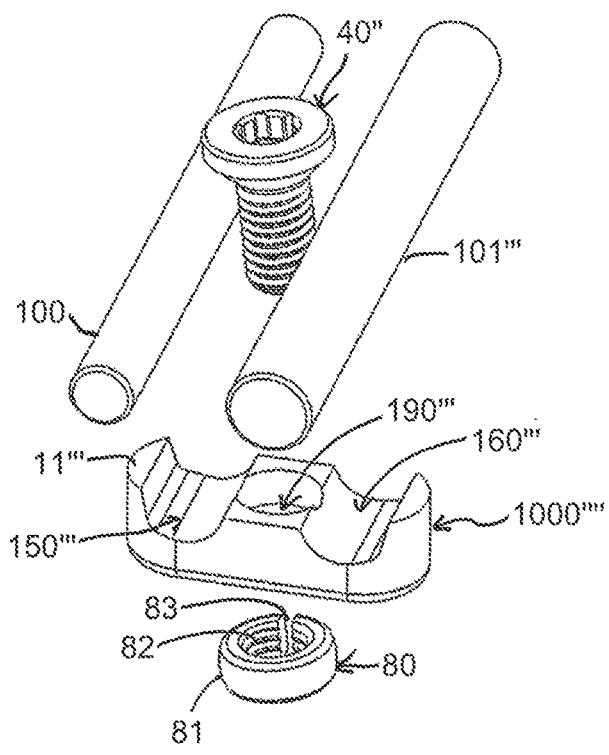
FIG. 44 shows a perspective exploded view of a rod system of a still further embodiment.
Figure 45:
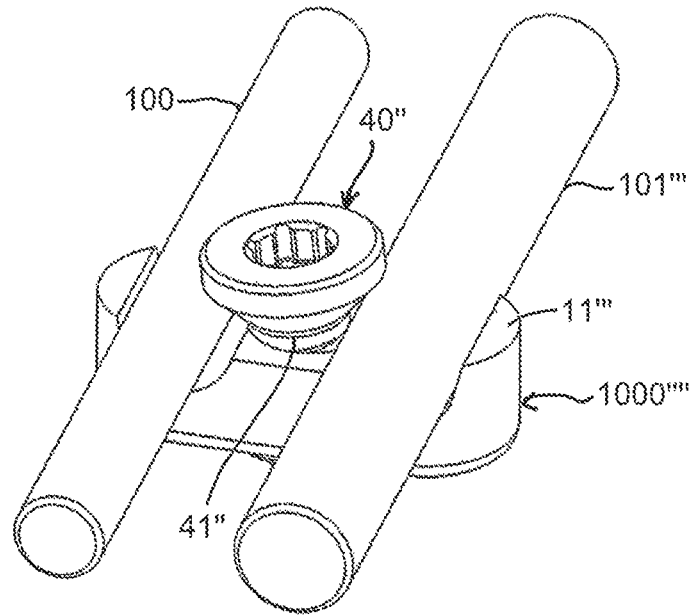
FIG. 45 shows a perspective view of the rod system of FIG. 44 in an assembled state.
Figure 46:
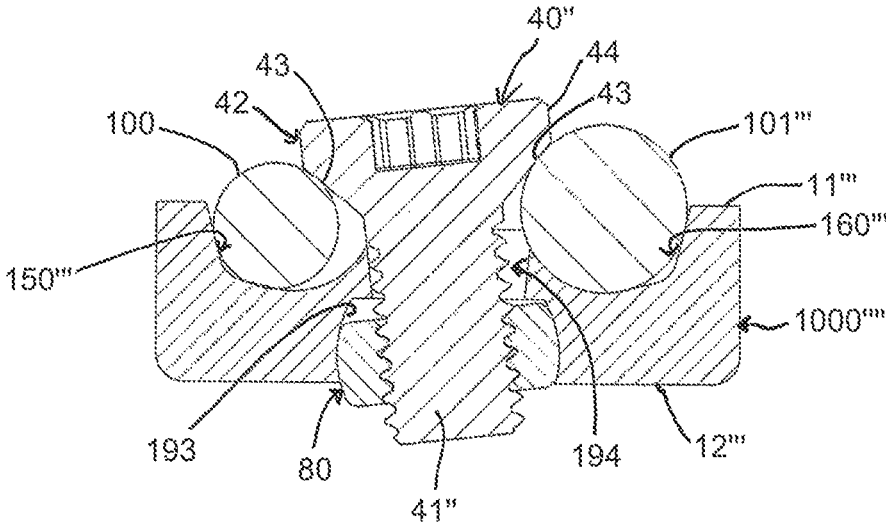
FIG. 46 shows a cross-sectional view of the rod system of FIGS. 44 to 45, the cross-section taken in a plane perpendicular to longitudinal axes of two inserted rods and extending through a center of a fixation member, wherein the rods have different diameters.

Referring to FIGS. 37 to 43, a still further embodiment of a rod system will be described. Parts and portions that are identical or similar to the previously described embodiments are marked with the same reference numerals, and the descriptions thereof will not be repeated. The rod system is configured to be used with various sets of rods, wherein the sets differ with respect to the diameter of the rods. The main body 1000'' is similar to the main body 1000'' of the previous embodiment, however, the rod seats 150''', 160'' are configured to receive rods of various diameters. For example, as shown in FIG. 38, the rod seats 150'', 160''' can receive a pair of rods 100, 101 of the same first diameter and can alternatively, as depicted in FIG. 39, receive a pair of rods 100', 101' of the same second diameter that is smaller than the first diameter. As depicted in FIGS. 40 to 43, the main body 1000'' has a top 11''', an opposite bottom 12'', sides 13''', 14''' which may be cylindrically-shaped and connect the top and the bottom, a front end 1000'''a, and a rear end 1000'''b. In the middle of the main body between the rod seats 150'' and 160''', an orifice 190''' is provided for receiving a fixation member 40'. The first rod seat 150''' includes a cylindrical portion 150'''a and a substantially V-shaped portion 150'''b (seen in cross-section), preferably with a rounded bottom that is connected to the cylindrical portion 150'''a in a continuous manner. The sidewalls of the V-shaped contour may form an angle between 45° and 135°, preferably around 90°. The cylindrical portion 150'''a is closer to the center of the main body or closer to the orifice in the width direction, whereas the V-shaped portion 150'''b is located closer to the side 13'''. Likewise, the second rod seat 160''' includes a cylindrical portion 160'''a arranged closer to the center of the main body in the width direction, and V-shaped portion 160'''b, preferably with a rounded bottom that is connected to the cylindrical portion 160'''a in a continuous manner and that is located closer to the side 14'' than the cylindrical portion 160'''a is to the side 14'''. The shape of the cylindrical section and of V-groove section of both rod seats may be identical and mirror symmetrical to a plane extending through the orifice 190''' in the height direction. The orifice 190''' includes a threaded portion 191'' adjacent to the bottom 12'' and a tapered portion 192''' adjacent to the top 11'''. In greater detail, the orifice 190''' is configured to receive the fixation member 40' which differs from the fixation member 40 in that the head 42 has an enlarged tapered surface 43' and may have a cylindrical portion 44' with an axially reduced height.

In use, when a first pair of rods 100, 101 is used that has a first diameter which may correspond to the inner diameter of the cylindrical portions 150'''a and 160'''a of the rod seats 150''', 160''', respectively, the rods may each substantially fill the rod seat except a small portion in the ground region of the V-shaped portion. When the fixation member 40' is inserted into the orifice 190''', the fixation member touches with the tapered portion 43' onto the upper side of both rods, while the threaded shaft 41 may not extend fully into the threaded portion 191''', as depicted in FIG. 38.

When a second pair of rods 100', 101' with a smaller diameter than the first diameter is used, the rods 100', 101' do not fully fill the rod seats in the cylindrical portion 150'''a, 160'''a, but rest on the flanks of the V-shaped portion 150'''b, 160'''b along substantially two contact areas that are substantially parallel to the longitudinal axes $I_1$, $I_2$ of the rod seats. Inserting and tightening the fixation member 40' against the rods 100', 101' allows the fixation member 40' to extend deeper into the threaded portion 191''', so that the tapered portion 43' of the head 42' of the fixation member 40' contacts the rods 100', 101' at a position farther outward in the radial direction of the head. The rods 100', 101' are firmly clamped along three contact areas, with two of the contact areas in the V-shaped portion of the rod seat and the third contact area at the tapered portion 43' of the fixation member 40'.

Lastly, a still further embodiment of the rod system will be described with reference to FIGS. 44 to 47.

The rod system according to this embodiment differs from the rod system according to the previous embodiment in that a pair of rods with different diameters can be used and fixed simultaneously with a single fixation member. A first rod 100'' has a smaller outer diameter compared to a second rod 101''. The main body 1000'' includes the first rod seat 150'' and the second rod seat 160''' as in the previous embodiment. The first rod 101'' is configured to be received in the first rod seat 150''' and the second rod 101'' is configured to be received in the second rod seat 160'''. The orifice 190'''' between the first rod seat 150'' and the second rod seat 160''' is configured to receive a fixation member 40'' and a pivot sleeve 80. The orifice 190'''' has, adjacent to the bottom 12'', a spherical segment-shaped recess 193 which includes a region of the sphere with a greatest diameter, i.e. over the equator of the sphere. The spherical segment-shaped recess 193 is configured to receive the pivot sleeve 80. The pivot sleeve 80 includes a spherical segment-shaped outer surface 81 and an inner cylindrical threaded passage 82 that is configured to cooperate with the threaded shank 41'' of the fixation member 40''. The pivot sleeve 80 further has an axial slot 83 that renders the pivot sleeve compressible and expandable. Adjacent to the spherical segment-shaped recess 193, a tapered, preferably conically-tapered, portion

194 is formed in the orifice 190'''' that widens towards the top 11''. The tapered portion 194 may have a smaller inner diameter adjacent the spherical segment-shaped recess 193 than an inner diameter of the spherical segment-shaped recess 193 adjacent the tapered portion. The tapered portion 194 permits the threaded shank 41'' to be tilted in the orifice 190''''. Similar to the fixation member 40 of the first embodiments, the head 42 of the fixation member 40'' includes a tapered section 43 and a cylindrical section 44.

The pivot sleeve 80 may be inserted into the main body 1000'''' by compressing it so that it can snap into the recess 193, where the pivot sleeve may be held by friction. Thereafter, the rods 100'' and 101'' may be placed in their respective rod seats 150''', 160'''. Finally, the fixation member 40'' is inserted into the orifice such that its shaft 41'' engages the threaded inner side 82 of the pivot sleeve 80. In this configuration, the fixation member 40'' can be tilted to some extent around its screw axis so that it can clamp both rods simultaneously, with the tapered portion 43 providing the third contact area for each of the rods that rest in the V-shaped portion of the rod seat, respectively.

Figure 47:
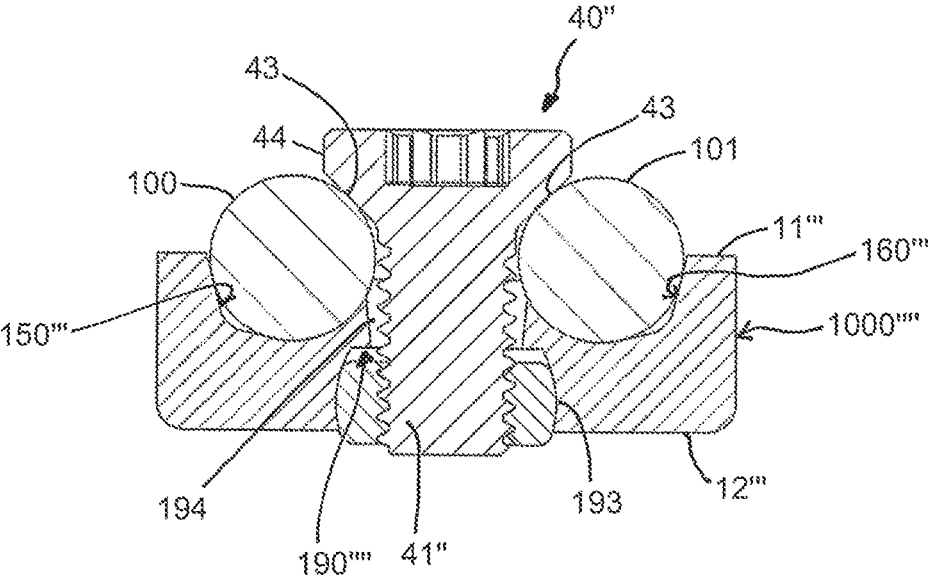
FIG. 47 shows a cross-sectional view of the rod system of FIGS. 44 to 45, with two rods having a same diameter.

In another mode of use, two rods 100, 101 of the same diameter are used, as shown in FIG. 47. In this case, the screw axis of the fixation member 40'' may be in the zero position, i.e. is perpendicular to an axis that extends along a width of the main body of the connector.

Modifications of the above described embodiments are also conceivable. The particular features, structures or characteristics of one embodiment may be combined with those of the other embodiments in any suitable manner to produce a multiplicity of further embodiments. Particular shapes of the elements are not limited to the specific shape shown in the drawings, but may vary. While straight rods are shown, the invention is not limited thereto. The rods may also have a curvature. Also, the rod seats and their respective longitudinal axes may have a curvature. Moreover, the rods can have another cross-section. The shape of the rod seat may be adapted to the cross-section of the rod. The orifices may also be closed at the bottom. Only one sliding member may be sufficient that may have any suitable shape. Also, the sliding members can be omitted.

For the bone anchoring elements that are not shown, all types of bone anchoring elements that are suitable for anchoring in a bone or a vertebra and configured to be connected to a rod may be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A rod system, in particular, for the spine, comprising:
a first rod;
a second rod; and
a connector for connecting the first rod and the second rod to one another, the connector comprising:
a main body defining a first rod seat that extends along a first longitudinal axis and that is configured to hold a portion of the first rod, a second rod seat that extends along a second longitudinal axis and that is configured to hold a portion of the second rod, and an orifice positioned between the first rod seat and the second rod seat, wherein a thread is formed in the orifice; and a monolithic fixation member comprising a threaded portion engageable with the thread formed in the orifice, a head that is wider than the threaded portion, and an engagement surface formed on the head that is configured to directly engage and hold both the first rod in the first rod seat and the second rod in the second rod seat relative to the main body.

2. The rod system of claim 1, wherein the fixation member is tiltable relative to an axis that is substantially perpendicular to the first and second longitudinal axes.

3. The rod system of claim 1, wherein the fixation member is configured to hold both the first rod and the second rod in a fixed manner relative to the main body.

4. The rod system of claim 1, wherein the longitudinal axes of the first rod seat and the second rod seat are substantially parallel to one another.

5. The rod system of claim 1, wherein the fixation member is movable translationally relative to the main body when the threaded portion of the fixation member engages the thread formed in the orifice of the main body.

6. The rod system of claim 1, wherein respective central axes of the first and second rods are configured to be located at a same axial position relative to a thread axis of the fixation member when the fixation member holds the first and second rods relative to the main body.

7. The rod system of claim 1, wherein the first and second rods have different diameters from one another.

8. A rod system, in particular, for the spine, comprising:
a first rod;
a second rod; and
a connector for connecting the first rod and the second rod to one another, the connector comprising:
  a main body defining a first rod seat that extends along a first longitudinal axis and that is configured to hold a portion of the first rod, a second rod seat that extends along a second longitudinal axis and that is configured to hold a portion of the second rod, and an orifice positioned between the first rod seat and the second rod seat; and a monolithic fixation member comprising an engagement surface engageable with an inner surface of the main body that defines the orifice, the fixation member being configured to directly engage both the first rod and the second rod to hold the first rod in the first rod seat and the second rod in the second rod seat relative to the main body, wherein the fixation member is tiltable relative to an axis that is substantially perpendicular to the first and second longitudinal axes.

9. The rod system of claim 8, wherein the fixation member comprises a threaded portion engageable with a thread formed in the orifice of the main body.

10. The rod system of claim 8, wherein the fixation member is configured to hold both the first rod and the second rod in a fixed manner relative to the main body.

11. The rod system of claim 8, wherein the first and second rods have different diameters from one another.

12. The rod system of claim 8, wherein the main body comprises a sleeve positionable in and pivotable relative to the orifice, and wherein the inner surface of the main body that is engageable with the engagement surface of the fixation member is formed on the pivot sleeve.

13. The rod system of claim 8, wherein the fixation member and the pivot sleeve are tiltable together relative to other portions of the main body.

* * * * *